United States Patent
Pan et al.

(10) Patent No.: US 7,799,353 B2
(45) Date of Patent: Sep. 21, 2010

(54) PHARMACEUTICAL MIXTURE FOR HEPATITIS TREATMENT AND ITS PREPARATION METHOD

(75) Inventors: I-Horng Pan, Hsinchu (TW); Yu-Ming Hsieh, Taichung (TW); Zhi-Jie Huang, Yuchih Township, Nantou County (TW); Hsi-Ho Chiu, Jhudong Township, Hsinchu County (TW); Chaur-Ting Ju, Hsinchu (TW); Chu-Hsun Lu, Kaohsiung (TW); Pei-Yi Tsai, Kaohsiung (TW); Wei-Lun Fan, Jhunan Township, Miaoli County (TW); Wen-Huang Peng, Dali (TW); Ming-Tsuen Hsieh, Taichung (TW)

(73) Assignee: Industrial Technology Research Institute (TW)

( * ) Notice: Subject to any disclaimer, the term of this patent is extended or adjusted under 35 U.S.C. 154(b) by 99 days.

(21) Appl. No.: 12/071,076

(22) Filed: Feb. 15, 2008

(65) Prior Publication Data
US 2008/0138445 A1  Jun. 12, 2008

Related U.S. Application Data

(63) Continuation of application No. 10/997,894, filed on Nov. 29, 2004, now Pat. No. 7,431,946.

(30) Foreign Application Priority Data
Dec. 30, 2003  (TW)  ............................. 92137522 A

(51) Int. Cl.
*A61K 36/00* (2006.01)

(52) U.S. Cl. ................................................. 424/725
(58) Field of Classification Search .................. None
See application file for complete search history.

(56) References Cited

OTHER PUBLICATIONS

Dechow, F. Separation and Purification Techniques in Biotechnology; 1989, Noyes Publications, Park Ridge, New Jersey, pp. 416 and 418.*
Nettle: Wikipedia Online: URL <http://en.wikipedia.org/wiki/Nettle> accessed Mar. 16, 2007, pp. 1-5.*
Remington et al. EXTRACTA; The Dispensatory of the United States of America, 1918, from Henriette's Herbal Pages URL <http://henriettesherbal.com/eclectic/usdisp/extracta.html> accessed Mar. 8, 2007, pp. 1-12 from Henriette's Herbal Pages.*
Animal Models (HBV0; Trimera Disease Model Developed for Hepatitis B; Cancerweekly Plus; Atlanta; Feb. 1999 pp. 1-2.*
Davis, G. Treatment of Chronic Hepatitis C; British Medical Journal; Nov. 2001, pp. 1-3.*

(Continued)

*Primary Examiner*—Patricia Leith
(74) *Attorney, Agent, or Firm*—Bacon & Thomas, PLLC

(57) ABSTRACT

A pharmaceutical mixture for the treatment of hepatitis and its preparation method are disclosed. The method includes the following steps: pulverize the plants, macerate and extract the plant with water, concentrate the aqueous extract as the first concentrate; add ethanol to form a precipitate, collect and concentrate the liquid phase to form the second concentrate, and dry it; pass the second concentrate through the resin, elute with water, water-ethanol mixture and ethanol, collect and concentrate the water-ethanol and ethanol elution fraction as the third concentrate, and dry it. The plants in the present invention are *Boehmeria frutescens* Thunberg, *Boehmeria nivea* or the nettle family.

11 Claims, 2 Drawing Sheets

(a) Control (b) d-Galactosamine (400mg/kg)

(c) Positive Control (Silymarin) (200mg/kg)

OTHER PUBLICATIONS

F. Dechow, Separation and Purification Techniques in Biotechnology, 1989, Noyes Publications, Park Ridge, New Jersey, pp. 416 and 418.

Remington, et al. EXTRACTA; The Dispensatory of the United States of America, 1918, from Henriette's Herbal Pages URL <http://www.henriettesherbal.com/eclectic/usdisp/extracta.html> accessed Mar. 8, 2007, pp. 1-12 from Henriette's Herbal Pages.

G. Davis, Treatment of Chronic Hepatitis C; British Medical Journal; Nov. 2001, pp. 1-3.

Chun-Ching Lin, et al., Evaluation of the hepatoprotective and antioxidant activity of *Boehmeria nivea* var. *nivea* and β. *Nivea* var. *tenacissima*; 1998; Journal of Ethnopharmacology; vol. 60; pp. 9-17.

Chun-Ching Lin et. al.; *Evaluation of the hepatoprotective and antioxidant activity of Boehmeria nivea* var. *nivea* and β. *Nivea* var. *tenacissima*; 1998; Journal of Ethnopharmacology; vol. 60; pp. 9-17.

\* cited by examiner (a) Control (b) d-Galactosamine (400mg/kg)

(c) Positive Control (Silymarin) (200mg/kg)

(d) Positive Control (Guanine) (300mg/kg)

(e) BMEC-1 (500mg/kg)

(f) BMEC-101 (50mg/kg)

PHARMACEUTICAL MIXTURE FOR HEPATITIS TREATMENT AND ITS PREPARATION METHOD

This application is a continuation application of pending U.S. patent application Ser. No. 10/997,894 filed Nov. 29, 2004 (of which the entire disclosure of the pending, prior application is hereby incorporated by reference).

BACKGROUND OF THE INVENTION

1. Field of the Invention

The present invention relates to a pharmaceutical mixture for hepatitis treatment and its preparation method, especially to a *Boehmeria* family plant for the treatment of hepatitis and preparation method of the same.

2. Description of Related Art

Chronic liver diseases (such as chronic hepatitis, cirrhosis, and liver cancer) have remained significant medical problems. Liver diseases include viral liver disease, alcoholic liver disease, drug or toxicant liver disease, and metabolism disorder liver disease. It is estimated that worldwide there are about 350 million people who are chronic B type hepatitis carriers, and 2.7 million people who are chronic C type hepatitis carriers. In Taiwan, the B type hepatitis carrying rate is about 15 to 20%, and the C type hepatitis carrying rate is about 2 to 4%.

On one hand, the current medicines for treating hepatitis, such as liver protecting drugs, antiviral drugs or immune regulators, certainly have curative effects but on the other hand, they have side effects and are expensive. For example, interleukins and Lamivudine® are used for treating B type hepatitis. The interleukins, which were approved by the U.S. FDA in 1992 for treating B type hepatitis, have only 20% positive response but patients experience severe side effects. Lamivudine®, which was approved by the FDA in 1998 for treating B type hepatitis, also has only a 17 to 33% positive response. Furthermore, Lamivudine® will easily cause the mutation of B type hepatitis virus, and thus its potency is reduced.

In Chinese communities, hepatitis is usually treated with a traditional prescription, i.e. a herbal-type medicine. The potency of that medicine, however, is not so good and has low reproducibility (probably due to lack of precise process control). Hence, there are still some problems that need to be overcome in the treatment of hepatitis.

The present invention provides a composition for effective treatment of hepatitis and a novel process of the same. Liver protection can be achieved in those drug-based or other chemical (alcoholic liver disease) hepatitis cases as well as the chronic hepatitis patients.

Traditional Chinese medicines are usually extracted by water extraction, but this method cannot obtain enough active components. In addition, the active components will lose their activity at a high extraction temperature. Many processes in preparing pharmaceutical mixtures for hepatitis treatment have been disclosed. However, the prior arts use complex materials and traditional processes, which have not been able to solve the above problems.

Alternatively, a process that utilizes organic solvents, such as methanol, acetone, and chloroform, to extract the active components, has been disclosed. These organic solvents are toxic and need to be removed completely before a patient can be treated. Therefore, it is desirable to provide a novel pharmaceutical mixture for hepatitis treatment and its preparation method.

In the present invention, it is observed that *Boehmeria* family plant is effective for treating hepatitis. However, from the above description, the efficacy of traditional oral extract is limited. Moreover, in the industry, the toxic organic solvents are usually adopted in the extraction process and the active component may decay. Therefore, it is desirable to provide a novel preparation process and *Boehmeria* family plant for treating hepatitis, and the components of the product are more efficacious than traditional ones. There are more active substances and better curative effects, but no toxic organic solvents are used in the process so as to promote drug safety.

SUMMARY OF THE INVENTION

The object of the present invention is to provide a pharmaceutical mixture for the treatment of hepatitis and its preparation method, which possesses the property of liver protection, and further serves as a drug for treating chronic hepatitis.

Another object of the present invention is to provide a pharmaceutical mixture for the treatment of hepatitis and its preparation method, wherein the active components are extracted from the composition without using of toxic organic solvents.

To achieve the object, the processes for preparing a pharmaceutical mixture for the treatment of hepatitis in the present invention are as follows: the plant is pulverized, macerated and extracted with water, and the aqueous extract is concentrated into a first concentrate; ethanol is added to form a precipitate, the liquid phase is collected and concentrated to form a second concentrate, and dried; wherein the plants are *Boehmeria frutescens* Thunberg, *Boehmeria nivea* or the nettle family.

The process for preparing a pharmaceutical mixture for the treatment of hepatitis in the present invention can further include: the second concentrate is passed through a resin, eluted with water, water-ethanol mixture and ethanol, the water-ethanol and ethanol elution fraction are collected and concentrated as a third concentrate, and dried.

The present invention also comprises a pharmaceutical mixture for the treatment of hepatitis according to the above-mentioned method. The components are extracted from *Boehmeria frutescens* Thunberg, *Boehmeria nivea* or the nettle family.

In the present pharmaceutical mixture for the treatment of hepatitis and its preparation method, the time for maceration has no limit, but preferably is 8-24 hrs; the extracting step further comprises a process of boiling and stirring for at least once, and each extract is collected to form the aqueous decoction; the first decoction is preferably concentrated to form the first concentrate of 1-50 wt % solid content; the preferred concentration of ethanol used for precipitation is 95 wt %, and the more preferred final concentration is 40 to 80 wt %; the separation of solid and liquid phase has no limit, and preferably is separated by centrifugation; and the preferred solid content of the second concentrate is 5-50 wt %.

In the further purification process of the present pharmaceutical mixture for treatment of hepatitis, stirring time and temperature are both without limit, and preferably are 0.5-5 hr and 15-60° C., the process for solid and liquid phase separation has no limit, and preferably is separated by centrifugation; the resin has no limit, and preferably is macroporous resin or ion exchange resin; ethanol concentration in the product elution is without limit, and preferably is 95-100% ethanol; the ratio of water-ethanol mixture is without limit, and preferably is 1:4 to 4:1; the third concentrate is preferably concentrated to 5-50 wt % solid content.

In the process of the present pharmaceutical mixture for the treatment of hepatitis, product drying has no limit, and preferably is dried by lyophilizing, spray and granulating drying, or fluidized-bed drying; and the process of the present invention further selectively dries, pulverizes, granulates and encapsulates the final product.

Other objects, advantages, and novel features of the invention will become more apparent from the following detailed description when taken in conjunction with the accompanying drawings.

BRIEF DESCRIPTION OF THE DRAWINGS

FIG. 1 shows the histopathological sections in which FIG. 1(a) is the Control

FIG. 1(b) shows the results for d-Galactosamine (400 mg/kg)

FIG. 1(c) shows the results for Positive Control (Silymarin) (200 mg/kg)

FIG. 1(d) shows the results for Positive Control (Guanine) (300 mg/kg)

FIG. 1(e) shows the results for BMEC-1 (500 g/kg)

FIG. 1(f) shows the results for BMEC-101 (50 mg/kg).

DETAILED DESCRIPTION OF THE PREFERRED EMBODIMENT

Embodiment 1

Preparation of *Boehmeria frutescens* Thunberg Extract—JM

Figure 1:
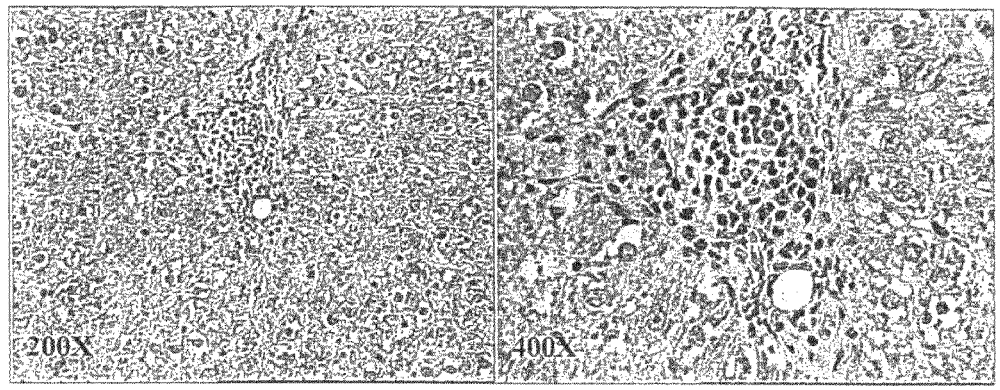
Figure 1:
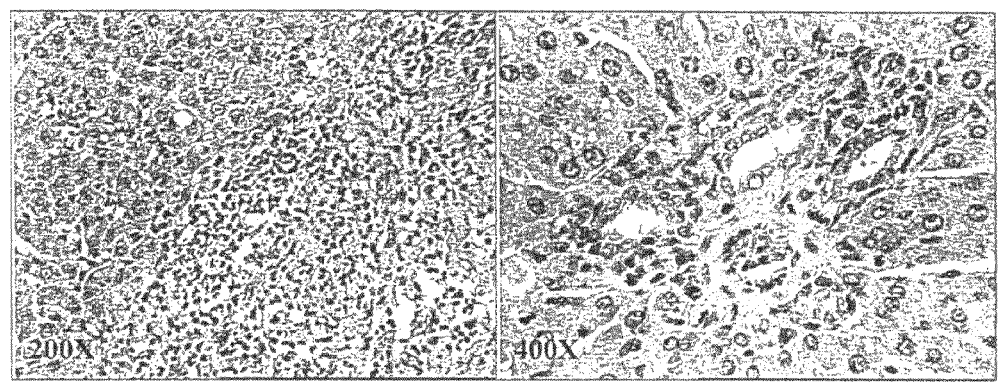
Figure 1:
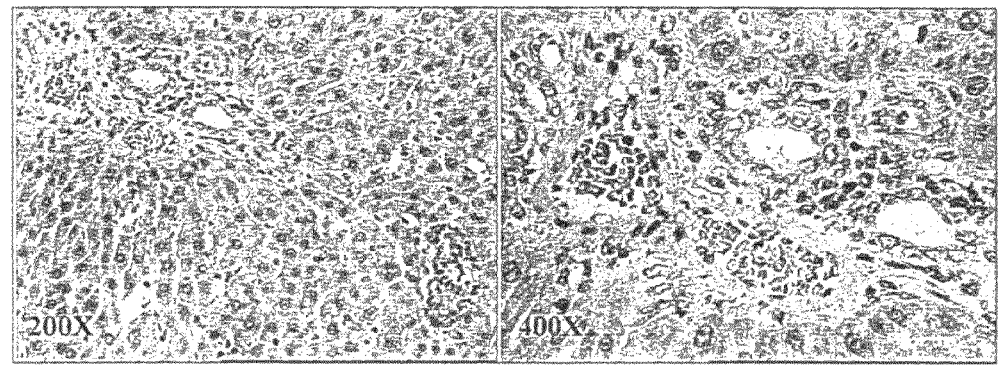
Figure 1:
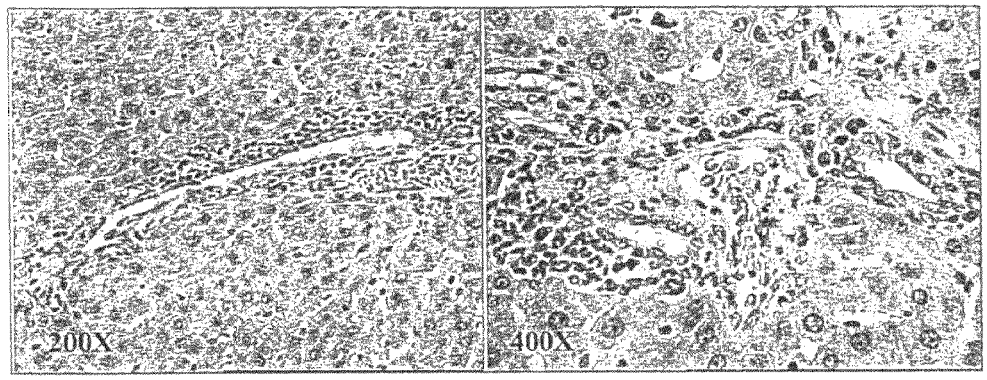
Figure 1:
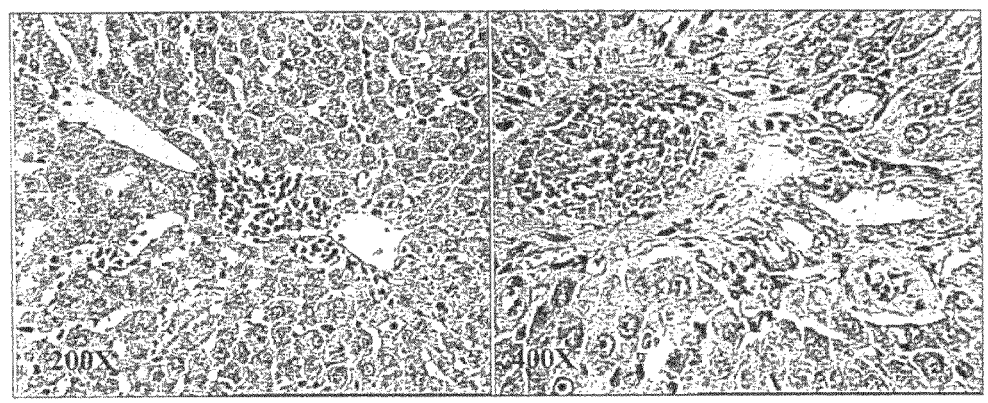
Figure 1:
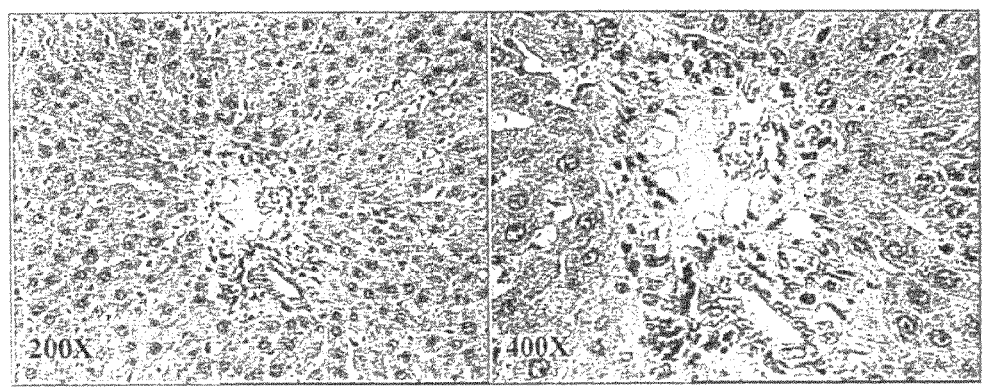

A 0.36 kg of *Boehmeria frutescens* Thunberg root is macerated in 3.6 kg water for 2 hr. After extraction at 100° C. for about 2 hr, the mixture is filtrated to form a decoction. Further, 2.2 kg of water is added for extraction at 100° C. for about 2 hr to form another decoction. The two decoctions are mixed and concentrated under reduced pressure to form a 0.218 kg concentrate with 15.3 wt % solid content. After lyophilization, the product JM is 33 g in weight.

Embodiment 2

Preparation of Partially Purified *Boehmeria frutescens* Thunberg Extract—BMEC-1

A 15 kg of *Boehmeria frutescens* Thunberg root is macerated in 150 kg water for 8-16 hr. After extraction at 100° C. for 2 hr, the mixture is filtrated to form the first decoction. Further, 150 kg of water is added for extraction at 100° C. for 2 hr to form the second decoction. The two decoctions are mixed into a 266 kg of decoction and concentrated under reduced pressure to form an 8.3 kg concentrate with 17.6 wt % solid content. The concentrate is stirred, and 15 L of 95% ethanol is added for ethanol precipitation by using a peristaltic pump. Finally, the ethanol precipitate is separated by a centrifuge, and the supernatant is collected, concentrated under reduced pressure, and lyophilized to form the product BMEC-1 with 1.013 kg in weight.

Embodiment 3

Preparation of *Boehmeria frutescens* Thunberg Extract—BMEC-101

A 95 kg of *Boehmeria frutescens* Thunberg root is macerated in the 800 kg water for 8-16 hr. After extraction at 100° C. for 2 hr, the mixture is filtrated to form the first decoction. Further, 700 kg of water is added for extraction at 100° C. for 2 hr to form the second decoction. The two decoctions are combined into a 1340 kg of decoction and concentrated under reduced pressure to form a 42 kg of concentrate with 25 wt % solid content (the first concentrate). Then, the concentrate is stirred, and 70 L of 95% ethanol is added for ethanol precipitation by using a peristaltic pump. The ethanol precipitate is separated by a centrifuge, and the supernatant is collected, concentrated under reduced pressure to form a 12.5 kg concentrate with 15 wt % solid content (the second concentrate). The solid phase and liquid phase of the second concentrate are separated by a centrifuge, and the supernatant is collected and passed through a HP20 resin column (macroporous, styrene serial adsorption/desorption resin), and then washed with 30 L of water. After eluting with 30 L of 50% ethanol (95% ethanol/water=1V/1V), a 29.1 kg of 50% ethanol elution fraction is obtained. Moreover, a 12.3 kg of ethanol elution fraction is obtained after eluting with 15 L of ethanol (95% ethanol). The 50% ethanol elution fraction and the ethanol elution fraction are collected and combined, and concentrated under reduced pressure to form a 1.9 kg concentrate with 21.6 wt % solid content (the third concentrate). The lyophilized product is 0.415 kg in weight, and coded as BMEC-101.

Embodiment 4

Comparison of the Purification Factor of Each Process

In Table 1, to begin with 100 kg of botanical raw material, the purification factor is increased up to 200 for BMEC-101 with those sequential purification procedures from extraction, ethanolic purification and resin purification.

TABLE 1

The relationship of product purification factors

| | | Product | | |
|---|---|---|---|---|
| | Botanical raw material | JM | BMEC-1 | BMEC-101 |
| Weight (kg) | 100 | 10 | 5 | 0.5 |
| Purification Factor | 1 | 10 | 20 | 200 |

Purification factor = Weight$_{botanical\ raw\ material}$/Weight$_{purified\ product\ JM,\ BMEC-1\ or\ BMEC-101}$

Embodiment 5

Animal Test (In Vivo)—d-galactosamine-Induced Acute Hepatitis (the Positive Control Group is Orally Given with Guanine)

Male rats are randomly divided, with five rats in the individual group and 200±20 g of each. In the study, normal and d-galactosamine (Gal) groups are orally given with distilled water, testing groups are orally given with test articles (JM or BMEC-1 from different processes) dissolving in distilled water, positive control group is orally given with guanine (300 mg/kg), and each administration dosage is 10 ml/kg.

Half-hour later, each group is i.p. with d-galactosamine (500 mg/kg) except the normal group. Four and eight hours after d-galactosamine injection, the same dosages are administrated again. Twenty-four hours after d-galactosamine injection, the animals are sacrificed for collecting the blood, and then the serum GOT (Glutamyl Oxaloacetic Transaminase) and GPT (Glutamyl Pyrubic Transaminase) activities are measured by using HITACHI auto-analyzing system (model 7050) with UV method.

Embodiment 6

Animal Test (In Vivo)—d-galactosamine-Induced Acute Hepatitis (Two Positive Control Groups are Orally Given with Silymarin and Guanine, Individually)

Rats are randomly divided, with six rats in each group. The animals fasted for 24 hr before the experiment. In the study, normal and d-galactosamine (Gal) groups are orally given with distilled water, testing groups are orally given with 1 g/kg of the test articles (JM, BMEC-1 or BMEC-101 from different processes) dissolving in distilled water, and rats in positive control group are orally administrated with silymarin (200 mg/kg) and guanine (300 mg/kg). One hour later, each group is i.p. with d-galactosamine (400 mg/kg), and the normal group is i.p. with saline. Four and eight hours after d-galactosamine injection, the same dosages are administrated again. Twenty-four hours after d-galactosamine injection, the animals are anesthetized with ether, and the blood is collected from the carotid artery. The serum is separated and stands still at room temperature for 1 hr, and centrifuged (Backman centrifuge, GS-6R, 3000 rpm) for 10 mins. The activities of rat serum GOT and GPT are measured.

Embodiment 7

Preparation of the Histopathological Sections

After blood is collected, the liver of the acute hepatitis animal induced by d-galactosamine is separated, and liver tissue around 0.5 cm$^3$ in each folium is taken out. Those tissues are fixed in 10% neutral formalin for 1 to 2 weeks, then dehydrated and paraffin embedded by the dehydration and wax-exudation device, and cut into 4 to 5 μm liver slices by rotary microtome. The slices are stained with Haematoxylin and Eosin, and the pathological patterns are observed under an optical microscope.

Embodiment 8

Experimental Results

When the hepatocytes are damaged, liver enzymes will be largely released to the blood stream whereby the serum GOT and GPT activities are elevated. Thus, mouse serum GOT and GPT variations can be compared before and after *Boehmeria frutescens* Thunberg extract treatment, to speculate the repairing effect of *Boehmeria frutescens* Thunberg extract on liver damage. Also, liver weights are compared to evaluate the liver swell situation. The results are as follows:

(a) Table 2 Shows the Hepaprotective Effect of *Boehmeria frutescens* Thunberg Extract (JM) on the d-galactosamine-Induced Acute Hepatitis in Rats

TABLE 2

The effect of *Boehmeria frutescens* Thunberg extract (JM) on the d-galactosamine - induced acute hepatitis in rats

| Groups | Dosage (mg/kg) | sGOT (U/L) | sGPT (U/L) |
|---|---|---|---|
| Normal | — | 180.0 ± 24.2 | 84.8 ± 8.9 |
| d-galactosamine (Gal) | 500 | 1298.0 ± 57.3 | 871.2 ± 58.9 |
| Gal + guanine | 300 × 3 | 980.0 ± 92.5*** | 589.6 ± 54.6*** |
| Gal + JM | 1000 × 3 | 849.6 ± 202.6** | 396.0 ± 59.2*** |

(Sample n = 5, value is represented as mean ± SEM, and compared with the d-galactosamine group with significant difference indicated by *p < 0.05, p < 0.01, and *p < 0.001 with student's t-test analysis.)

High serum GOT and GPT activities induced by d-galactosamine are reduced significantly after *Boehmeria frutescens* Thunberg extract (JM) treatment (the reduction of sGOT and sGPT values are 35% and 55%, individually). The positive control group is compared (orally given with guanine, and sGOT and sGPT values are reduced 24% and 32%, individually) to evaluate the protection or repairing function of JM in the liver damage induced by d-galactosamine.

(b) Table 3 Shows the Hepaprotective Effect of *Boehmeria frutescens* Thunberg Extract (BMEC-1) on the d-galactosamine-Induced Acute Hepatitis in Rats

TABLE 3

The effect of *Boehmeria frutescens* Thunberg extract (BMEC-1) on the d-galactosamine - induced acute hepatitis in rats

| Group | Dosage (mg/kg) | sGOT (U/L) | sGPT (U/L) |
|---|---|---|---|
| Normal | — | 110.4 ± 8.2 | 39.6 ± 1.3 |
| d-galactosamine (Gal) | 500 | 1727.6 ± 182.9 | 1255.2 ± 125.1 |
| Gal + guanine | 300 × 3 | 954.8 ± 122.1*** | 514.4 ± 78.2*** |
| Gal + BMEC-1 | 1000 × 3 | 618.4 ± 102.8*** | 414.0 ± 67.6*** |

(Sample n = 5, value is represented as mean ± SEM, and compared with the d-galactosamine group with significant difference indicated by *p < 0.05, p < 0.01, and *p < 0.001 with student's t-test analysis.)

After orally administrating 1000×3 mg/kg *Boehmeria frutescens* Thunberg extract (BMEC-1) prepared from the Embodiment 2, the high serum GOT and GPT values induced by d-galactosamine are significantly reduced (the reduction of sGOT and sGPT values are 64% and 67%, individually). The positive control group is compared (orally given 300×3 mg/kg guanine, and sGOT and sGPT values are reduced by 45% and 59%, individually) to evaluate the protection and repairing functions of BMEC-1 in preventing d-galactosamine-induced liver damage.

(c) Table 4 Shows the Effects of Different Batches of *Boehmeria frutescens* Thunberg Extract (BMEC-1) and Dose Dependence on the d-galactosamine-Induced Acute Hepatitis in Rats To understand the reproducibility of BMEC-1 preparation process from the Embodiment 2, two continuous batches were produced using the process from the Embodiment 2. The consistency of the two batches is observed, and the protection efficacy of d-galactosamine-induced acute hepatitis with treatment of different dosages is examined. The result is described in Table 4.

TABLE 4

Effects of different batches of *Boehmeria frutescens* Thunberg extract (BMEC-1) and dose dependence effect on the d-galactosamine - induced acute hepatitis in rats

| Batch 1 | Dosage (mg/kg) | sGOT (U/L) | sGPT (U/L) |
|---|---|---|---|
| Normal | — | 140.8 ± 11.6 | 41.2 ± 3.2 |
| d-galactosamine (Gal) | 500 | 2054.8 ± 227.9 | 1187.6 ± 156.8 |
| Gal + guanine | 300 × 3 | 1055.6 ± 150.1*** | 699.2 ± 103.6*** |
| Gal + BMEC-1 | 1000 × 3 | 887.6 ± 120.1*** | 478.4 ± 70.4*** |
| Gal + BMEC-1 | 300 × 3 | 1132.4 ± 143.0*** | 780.8 ± 80.2** |
| Gal + BMEC-1 | 100 × 3 | 1623.2 ± 165.5** | 906.4 ± 73.4* |

| Batch 2 | Dosage (mg/kg) | GOT (U/L) | GPT (U/L) |
|---|---|---|---|
| Normal | — | 123.6 ± 4.7 | 32.0 ± 2.8 |
| d-galactosamine (Gal) | 500 | 1872.8 ± 246.6 | 1137.2 ± 125.4 |
| Gal + guanine | 300 × 3 | 1080.0 ± 181.7*** | 584.0 ± 114.9*** |
| Gal + BMEC-1 | 1000 × 3 | 966.4 ± 151.6*** | 525.6 ± 101.1*** |
| Gal + BMEC-1 | 300 × 3 | 1238.0 ± 164.1** | 646.8 ± 86.5** |
| Gal + BMEC-1 | 100 × 3 | 1645.2 ± 185.6 | 995.6 ± 117.7 |

(Sample n = 5, value is represented as mean ± SEM, and compared with the d-galactosamine group with significant difference indicated by $*p < 0.05$, $p < 0.01$, and $*p < 0.001$ with student's t-test analysis.)

After orally administrating (1000×3 mg/kg) *Boehmeria frutescens* Thunberg extract (coded BMEC-1) prepared from the Embodiment 2 (Batch 1), the high serum GOT and GPT values induced by d-galactosamine are significantly reduced (the reduction of sGOT and sGPT values are 57% and 60%, individually). The positive control group is compared (orally given 300×3 mg/kg guanine, and sGOT and sGPT values are reduced by 49% and 41%, individually).

Similarly, after orally administrating (1000×3 mg/kg) with *Boehmeria frutescens* Thunberg extract (coded BMEC-1) prepared from the Embodiment 2 (Batch 2), the high serum GOT and GPT values induced by d-galactosamine are significantly reduced (the reduction of sGOT and sGPT values are 48% and 54%, individually). The positive control group is compared (orally given 300×3 mg/kg guanine, and sGOT and sGPT values are reduced by 42% and 49%, individually).

Accordingly, for the liver protection and repairing, both batches of the ethanol-precipitated supernatant of *Boehmeria frutescens* Thunberg extract (BMEC-1) can effectively prevent the d-galactosamine-induced liver damage.

In the dose dependence evaluation study, the examined data of those two batches both show a dose dependence decrease of serum sGOT and sGPT by BMEC-1 administration (three dosages: 100×3 mg/kg, 300×3 mg/kg, and 1000×3 mg/kg).

(d) Table 5 Shows the Effect of *Boehmeria frutescens* Thunberg Extract (BMEC-101) Prepared from Further Purification Process (Embodiment 3) and Dose Dependence Effect on the d-galactosamine-Induced Acute Hepatitis in Rats.

To effectively retain and concentrate the active components of *Boehmeria frutescens* Thunberg extract, and to largely reduce the therapeutic dose, the present invention further modifies the process of the Embodiment 2 into the Embodiment 3, to provide a more active composition. The above-mentioned active composition is used in the treatment of d-galactosamine-induced acute hepatitis in rats, and the result is shown in Table 5.

TABLE 5

The effect of *Boehmeria frutescens* Thunberg extract (BMEC-101) prepared from further purification process on the d-galactosamine - induced acute hepatitis in rats

| Group | Dosage (mg/kg) | sGOT (U/L) | sGPT (U/L) |
|---|---|---|---|
| Normal | — | 131.2 ± 2.0 | 43.6 ± 4.6 |
| d-galactosamine (Gal) | 400 | 528.8 ± 66.3 | 259.6 ± 42.2 |
| Gal + guanine | 300 × 3 | 160.7 ± 33.5** | 55.1 ± 19.2* |
| Gal + silymarin | 200 × 3 | 153.8 ± 8.9*** | 31.1 ± 1.3** |
| Gal + BMEC-1 | 500 × 3 | 280.9 ± 31.9 | 150.1 ± 19.8 |
| Gal + BMEC-101 | 50 × 3 | 106.0 ± 3.3*** | 37.2 ± 4.8** |

(Sample n = 6, value is represented as mean ± SEM, and compared with the d-galactosamine group with significant difference indicated by $*p < 0.05$, $p < 0.01$, and $*p < 0.001$, after Sheffe's test, the sample is analyzed with one-way ANOVA.)

After orally administrating (50×3 mg/kg) product (BMEC-101), the high serum GOT and GPT values induced by d-galactosamine are significantly reduced (the reduction of sGOT and sGPT values are 80% and 86%, individually). The positive control groups are compared (orally administrated 300×3 mg/kg guanine, and sGOT and sGPT values are reduced by 70% and 79%, individually; orally administrated 200×3 mg/kg silymarin, and sGOT and sGPT values are reduced by 71% and 88%, individually). Accordingly, it is shown that the product (BMEC-101) of the present process of the Embodiment 3 can possess the liver protection and repairing functions. Moreover, the therapeutic dose is only 50×3 mg/kg compared with the 200×3 mg/kg silymarin, and the 300×3 mg/kg guanine as positive control, it is shown that BMEC-101 possess a better liver protection potency than silymarin. It is also shown that BMEC-101 is more potent in liver protection than BMEC-1 with much lower dosage.

(e) Result of Histopathological Examination

TABLE 6

The report of the histopathological sections

| Histo-pathological examination | Normal | Gal | Silymarin 200 mg/kg | Guanine 300 mg/kg | BMEC-1 500 mg/kg | BMEC-101 50 mg/kg |
|---|---|---|---|---|---|---|
| Inflammation | 1 | 3 | 1 | 1 | 2 | 1 |
| Necrosis | 0 | 3 | 0 | 0 | 2 | 0 |
| Fatty change | 0 | 1 | 1 | 1 | 1 | 1 |
| Balloon degeneration | 0 | 0 | 0 | 0 | 0 | 0 |
| Bile duct proliferation | 0 | 3 | 2 | 1 | 2 | 2 |
| Mitosis | 0 | 0 | 0 | 0 | 0 | 0 |
| Fibrosis | 0 | 2 | 1 | 1 | 1 | 1 |

(The evaluation of liver damage: 0 = absent; 1 = trace; 2 = weak; 3 = moderate; 4 = strong.)

(The evaluation of liver fibrosis: 0=normal; 1=proliferation of collagen fibrosis without forming a septum; 2=central vein and portal zone are separated; 3=an intact septum is formed with a crossing in the middle, and the liver is substantially separated into several fractions but the septum is still thin; 4=an intact septum is formed and the septum becomes thick, liver cirrhosis.)

According to Table 6 and FIG. 1, it is shown that the negative control group, d-galactosamine (Gal) induced liver damage, results in cell inflammation, cell necrosis and bile duct proliferation (FIG. 1b). Also, a mild fatty change and a liver fibrosis in the middle of central vein and portal zone are observed. In the comparison among the test groups (BMEC-1 as FIG. 1e, and BMEC-101 as FIG. 1f), the positive control group (silymarin as FIG. 1c, and guanine as FIG. 1d) and the negative control group (d-galactosamine as FIG. 1b), Table 6 and FIG. 1 indicate that both BMEC-101 and BMEC-1 do not have damage in terms of ballooning degeneration and mitosis. Moreover, the therapeutic dose of BMEC-101 is only 50 mg/kg, and compared with the silymarin (200 mg/kg) and the guanine (300 mg/kg), it is shown that BMEC-101 possesses a better liver protection than that of the silymarin. Also, it is shown that the active component is effectively retained and concentrated so as to obtain the desired effect. For the fatty change, liver fibrosis, cell inflammation, cell necrosis and bile duct proliferation, BMEC-101 and BMEC-1 are both identical to the positive control group. In the comparison with the negative control group, only a mild or weak damage occurs in both of them.

From the above results, it is known that the *Boehmeria frutescens* Thunberg extract prepared from the present invention can significantly reduce serum GOT and GPT activities, namely, repair liver damage. Moreover, a low dose can achieve the desired effect, which also indicates an effective retaining and concentration of the active component from *Boehmeria frutescens* Thunberg extract. It is known that the preparation method of the present invention is not only a novelty but also capable of largely extracting the effective substance, and thus able to completely keep it from losing the activity.

In addition, without using toxic organic solvents, the extraction method of the present invention utilize ethanol and water only, which are harmless to the human body. And, those skilled in this art realize that applying the alcohol extraction can scarcely obtain extract with high potency. However, with further studies and several experiments by the inventor, the alcohol concentrations used to extract maximum amounts of effective components are obtained, and the animal study also verifies their particular efficacy. The disclosure of the present art means an avoidance of the toxic solvents such as methanol, chloroform, or acetone to obtain a desired product for the hepatitis therapy.

Although the present invention has been explained in relation to its preferred embodiment, it is to be understood that many other possible modifications and variations can be made without departing from the spirit and scope of the invention as hereinafter claimed.

What is claimed is:

1. A hepatoprotective mixture prepared by a method comprising the following steps:
    (a) pulverizing a plant, macerating and extracting the plant with water to form an aqueous extract, wherein said plant is *Boehmeria frutescens* Thunberg or *Boehmeria nivea*;
    (b) concentrating the aqueous extract to form a first concentrate;
    (c) adding ethanol to said first concentrate to produce a precipitate and a liquid phase;
    (d) collecting and concentrating said liquid phase to form a second concentrate;
    (e) purifying said second concentrate with a macroporous, styrene serial adsorption/desorption resin by loading said second concentrate onto the resin and eluting the resin with water, water-ethanol mixture, and then ethanol;
    (f) collecting and combining the water-ethanol and ethanol elution fraction; and
    (g) concentrating said combined elution fraction to form a third concentrate.

2. The hepatoprotective mixture as claimed in claim 1, wherein said plant is macerated with water for 8-24 hr in the step (a).

3. The hepatoprotective mixture as claimed in claim 1, wherein the plant is macerated and extracted repeatedly to form the aqueous extract in the step (a).

4. The hepatoprotective mixture as claimed in claim 1, wherein said aqueous extract is concentrated in said step (b) until solid content of the first concentrate reaches 1-50 wt %.

5. The hepatoprotective mixture as claimed in claim 1, wherein the initial concentration of said ethanol in step (c) is 95%.

6. The hepatoprotective mixture as claimed in claim 1, wherein said precipitate and said liquid phase of step (c) are separated by centrifugal filtration.

7. The hepatoprotective mixture as claimed in claim 1, wherein said liquid phase is concentrated in the step (d) until solid content of the second concentrate reaches 5-50 wt %.

8. The hepatoprotective mixture as claimed in claim 1, after the step (g) further comprising a step (h) of drying and pulverizing said third concentrate.

9. The hepatoprotective mixture as claimed in claim 8, wherein said drying method in the step (h) is lyophilizing, spray and granulating drying, or fluidized-bed drying.

10. The hepatoprotective mixture as claimed in claim 1, wherein the water-ethanol mixture in the step (e) has a concentration of 40-80 wt % ethanol.

11. A pharmaceutical composition having a hepatoprotective effect containing a hepatoprotective effective amount of the mixture of claim 1.

* * * * *